United States Patent [19]

Kisfaludy et al.

[11] 4,172,130
[45] Oct. 23, 1979

[54] α-AMINOACYL CONTAINING NEW PEPTIDES WITH GASTRIN EFFECTS AND A PROCESS FOR THE PREPARATION THEREOF

[75] Inventors: Lajos Kisfaludy; István Schön, both of Budapest; Vince Varró, Szeged; László Varga, Szeged; József Náfrádi, Szeged, all of Hungary

[73] Assignee: Richter Gedeon Vegyeszeti Gyar RT, Budapest, Hungary

[21] Appl. No.: 865,503

[22] Filed: Dec. 29, 1977

[30] Foreign Application Priority Data

Dec. 30, 1976 [HU] Hungary .................................. RI 608

[51] Int. Cl.² ...................... A61K 37/00; C07C 103/52
[52] U.S. Cl. ............................... 424/177; 260/112.5 R
[58] Field of Search ................... 424/177; 260/112.5 R

[56] References Cited

U.S. PATENT DOCUMENTS 3,896,103  7/1975  Hardy et al. .......................... 424/177

*Primary Examiner*—Delbert R. Phillips
*Attorney, Agent, or Firm*—Karl F. Ross

[57] ABSTRACT

Peptides of the formula:

A—Trp—B—Asp—Phe—NH—Y wherein A is tert.-butoxycarbonyl-aminooxy-acyl, benzyloxycarbonyl-aminooxy-acyl, (aminooxy)-acyl, or E-aminooxy-acyl, wherein E is benzoyl or straight-chain or branched $C_{1-5}$ aliphatic acyl, B is methionyl, leucyl, norleucyl, norvalyl or 2-amino-decanoyl, and Y is hydrogen or carboxymethoxy, and pharmaceutically acceptable acid-addition salts or complexes thereof have gastric-acid secretion increasing effects.

19 Claims, No Drawings

α-AMINOACYL CONTAINING NEW PEPTIDES WITH GASTRIN EFFECTS AND A PROCESS FOR THE PREPARATION THEREOF

The invention relates to α-aminooxyacyl-containing new peptides with gastrin effects, pharmaceutical compositions containing the same, and process for the preparation thereof.

The new peptides according to the invention have the formula (I), $$A-Trp-B-Asp-Phe-NH-Y \qquad (I)$$

wherein

A is tert.-butoxycarbonyl-aminooxy-acyl, benzyloxycarbonyl-aminooxy-acyl, (aminooxy)-acyl or E-aminooxy-acyl, wherein E is benzoyl or straight-chain or branched $C_{1-5}$aliphatic acyl, preferably formyl, acetyl or pivaloyl, B is methionyl, leucyl, norleucyl, norvalyl or 2-amino-decanoyl, and Y is hydrogen or carboxymethoxy.

The acid-addition salts and complexes of the above peptides are also within the scope of the invention.

The term "acyl", used in connection with the definition of substituent A, represents preferably a lower aliphatic acyl group, particularly acetyl or propionyl group.

As known, the biologically active center of gastrin, a peptide hormone consisting of 17 amino acids which stimulates gastric acid secretion, is the carboxy-terminal tetrapeptide-amide of the formula H—Trp—Met—Asp—Phe—NH$_2$. The gastric acid secretion stimulating effect of this tetrapeptide-amine is lower by about one order of magnitude than that of the total hormone. Several methods are known to synthesize the tetrapeptide-amide H—Trp—Met—Asp—Phe—NH$_2$ (J. C. Anderson et al.: J. Chem. Soc. C 108 (1967) Smirnov et al.: Khimia prirodnykh soedinenii 7, 94 (1971); Portelli, M. and Renzi, G.: Borin, G. E.: I. Farmaco Ed. Sci. 28, 332 (1973); J. M. Davey et al.: J. Chem. Soc. C 555 (1966); Hungarian patent specification No. 153,299; M. Dabrowska et al.: Roczniki Chemii 46, 1295 (1972). More than a hundred analogs and substituted derivatives of the above tetrapeptide-amine have also been described (J. M. Davey et al.: J. Chem. Soc. C 555 (1966); J. S. Morley: Proc. Roy. Soc. 170B, 97 (1968); M. Portelli and G. Renzi: Il Pharmaco Ed. Sci. 28, 316 (1973); Hungarian patent specification No. 153,375). Of these compounds the pentapeptide-amide of the formula BOC—β—Ala—Trp—Met—Asp—Phe—NH$_2$, the most active derivative, is available under the name "pentagastrin" and is used as a diagnostic agent in the determination of the maximum gastric acid secretion ability.

Several analogs of pentagastrin and the above tetrapeptide-amide have been described, in which some of the amino acids are replaced by others (J. Morley: Proc. Roy. Soc. 170B, 97 (1968); E. Wünsch and K.-H. Deimer: Hoppe-Seyler's Z. Physiol.Chem. 353, 1246 (1972); Morley et al.: J. Chem. Soc. C 522, 726, 910, 809, 715 (1968); Kenner et al.: J. Chem. Soc. C 762 (1968); A. von Dungen et al.: Liebigs Ann. Chem. 860 (1976); Japanese patent specification No. 71 17,234; Japanese patent specification No. 16,743/1971). All of these compounds are, however, less active than pentagastrin.

It is known that peptides containing α-(aminooxy)-carboxylic acids resist the effects of numerous proteolytic enzymes (L. Kisfaludy, M. Löw, T. Dévényi: Acta Biochim. Biophys. Acad. Sci. Hung. 6, 393 (1971). Thus e.g. the protracted effects of ACTH analogs containing an α-(aminooxy)-carboxylic acid on the terminal amino group can be attributed to the fact that the α-(aminooxy)-acyl group protects the molecule against the attacks of aminopeptidase type enzymes (Hungarian patent specification No. 167,655).

Now it has been found that pentagastrin analogs containing an (aminooxy)-carboxylic acid on the terminal amino group are very active compounds; the activities of the (aminooxy)-acetyl, α-L- and -D-(aminooxy)-propionyl- and β-(aminooxy)-propionyl derivatives are particularly remarkable. Some of these derivatives are more active than pentagastrin itself.

The new compounds of formula (I) can be prepared according to the invention by reacting a compound of formula (II), $$H-Trp-B-Asp-Phe-NH-Y \qquad (II)$$

wherein B and Y are as defined above, with a compound containing an (aminooxy)-acyl group and having the formula A$_1$—X, wherein A$_1$ has the same meanings as A with the exception of the (aminooxy)-acyl group, and X represents hydroxy group, halogen atom (preferably chlorine atom), pivaloyloxy group, a group of formula R—O—CO$_2$—(wherein R is lower alkyl group, preferably ethyl or isobutyl group), a phenoxy group having optionally a nitro substituent or one or more halogen substituent(s) (preferably p-nitrophenoxy, 2,4,6-trichlorophenoxy, 2,3,5-trichlorophenoxy, pentachlorophenoxy or pentafluorophenoxy group) or N-succinimidoxy group.

When a compound of formula A$_1$—X, wherein X is a hydroxy group, is used as reactant, the acylation is performed preferably in the presence of dicyclohexyl carbodiimide.

If desired, a compound of formula (I) is converted into its pharmaceutically acceptable acid-addition salt or complex, or a salt is converted into another pharmaceutically acceptable salt or inner salt, or a free acid of formula (I) is liberated from its salt.

The preferred reactants of formula A$_1$—X are mixed anhydrides or active esters formed with pivaloic acid or a carbonic acid-hemiester. Of the latter compounds the halogenated phenylesters, primarily the pentachlorophenyl and pentafluorophenyl esters, are particularly preferable.

The tetrapeptide-amides of the formula H—Trp—B—Asp—Phe—NH—Y, used as starting substances, can be prepared by fragment condensation or stepwise condensation according to methods known in the art. Of these methods e.g. the azide, mixed anhydride, dicyclohexyl carbodiimide and activated ester methods are to be mentioned.

If necessary, the functional groups not participating in the reaction are protected with appropriate blocking groups. Of the blocking groups, those which can be removed by hydrolysis, acidolysis or catalytic hydrogenation are preferred. Carboxy groups can be protected e.g. by esterifying with benzylalcohol, tert.-butanol or p-chloro-benzylalcohol, whereas formyl, tosyl, trityl, trifluoroacetyl, o-nitro-sulfenyl, phthalyl and p-chloro-carbobenzoxy groups, particularly carbobenzoxy and tert.-butoxycarbonyl groups, can be used to protect aminooxy and amino groups. The nitrogen atom of the indole skeleton of tryptophan can be protected with formyl group.

By the proper selection of the blocking groups compounds can be prepared which can be deblocked in a single step, or from which the blocking groups can be split off selectively by methods known in the art, such as hydrolysis, acidolysis, catalytic hydrogenation, etc.

According to a preferred method of the invention the pentahalophenyl ester method is used to introduce the protected N-terminal (aminooxy)-acyl group into the molecule. In this instance the active ester is reacted with the C-terminal H—Trp—B—Asp—Phe—NH—Y.

The tetrapeptide-amide H—Trp—B—Asp—Phe—$NH_2$ is prepared from Z—Phe—OH, by converting it first into Z—Phe—$NH_2$ by methods known in the art. Thereafter the protecting group is split off and the C-terminal tetrapeptide-amide (H—Trp—B—Asp—Phe—$NH_2$) is built up stepwise, using the appropriate protected amino acid(N-hydroxysuccinimide) esters or -pentahalophenyl esters.

The compound H—Trp—B—Asp—Phe—NH—O—$CH_2$—$CO_2$H is prepared from H—Phe—O—Gly—OH. This latter compound can be prepared by acylating (aminooxy)-acetic acid with a mixed anhydride or activated ester of Z—Phe—OH, and treating the resulting compound with hydrogen bromide in glacial acetic acid in order to remove the blocking group.

BOC—Phe—OH can also be used as a starting substance in the above two synthesis methods. The protecting group (BOC) can be removed from the compounds BOC—Phe—$NH_2$ and BOC—Phe—OGly—OH by treatment with an acid under less severe conditions.

The ester bond protecting the $\beta$-carboxy group of aspartic acid can be split off selectively in the dipeptide, tripeptide or tetrapeptide stage. This blocking group can also be split off along with the amino blocking group by acidolysis or, when Y is other than hydrogen, by catalytic hydrogenolysis.

The end-products can be purified by simple recrystallization, precipitation, column chromatography on silica gel or ion exchange chromatography on carboxymethyl cellulose.

Depending on their methods of preparation, the new compounds are obtained either as free acids or in the form of salts. the salts formed with organic or mineral acids can be converted into inner salts either by methods known per se or as a result of the purifying procedure.

The biological activities of the new compounds according to the invention were tested by the methods of Ghosh and Schild (Br. J. Pharmac. Chemoth. 13, 54 (1958) and Lai (Gut. 5, 327 (1964), modified by Pissidis and Clark (Gut. 8, 196 (1967)). The pharmacological tests have shown that the gastric acid secretion provoked by the new compounds is occasionally higher by 20 to 80% than that provoked by the same dosage of pentagastrin. It is particularly remarkable that the new compounds, in contrast with pentagastrin, are resorbed also from the small intenstine, and, when administered to the small intenstine in a dosage of 20 µg/100 g body weight, exert effects similar to that exerted by a 0.2 µg/100 g i.v. dosage of pentagastrin. In contrast thereto, pentagastrin does not increase the gastric acid secretion when administered enterally even in higher dosages. It is also remarkable that some of the new compounds increase the gastric acid secretion after resorption from the rectum. Taking into account that the new compounds are active after resorption from the small intestines and rectum, and are sometimes more active than pentagastrin, they can be used in a new and advantageous manner in the diagnostics and therapy.

The activity and resorption data of the new compounds according to the invention are summarized in Table 1.

Table 1

Gastric acid secretion increasing effects of the new compounds, administered enterally or parenterally, in comparison with that of a 0.2 µ/100 g i.v. dosage of pentagastrin

| Compound | | | Activity, % | | | |
| A | B | Y | 0.2 µg i.v. | 2.0 µg i.v. | 20 µg intestinal | 20 µg rectal |
| --- | --- | --- | --- | --- | --- | --- |
| BOC-OGly | Met | H | 142 | 294 | 51[x] | — |
| BOC-OGly | Leu | H | 124 | 272 | 6 | 68 |
| H-OGly | Met | H | 91 | 230 | 47[x] | 261 |
| BOC-L-OAla | Met | H | 66 | 94 | 59 | 33 |
| BOC-D-OAla | Leu | H | 140 | 240 | 35 | 49 |
| BOC-L-OAla | Met | OGly-OH | 56 | — | — | 18 |
| BOC-D-OAla | Met | OGly-OH | 66 | — | — | 104 |
| BOC-$\beta$-OAla | Met | OGly-OH | 32 | — | — | — |
| BOC-O-Gly | Met | OGly-OH | 25 | — | — | 22 |

[x]Administered in a dosage of 10/µg/100 g body weight
Pentagastrin = 100% i.v.

The term "pharmaceutically acceptable complexes" refers to comoounds of the novel peptides formed with certain organic or mineral substances, which impart protracted effects to the peptides. Of these organic substances e.g. certain gelatine types, carboxymethyl celluloses, alginic acid esters, poly(floretine-phosphate), amino acid polymers or other polymers and copolymers are to be mentioned. Of the inorganic substances hydroxides and relatively insoluble salts (such as phosphates and pyrophosphates) of certain metals (such as zinc) can be used. The above effect can also be attained with certain silicates, which form water-insoluble complexes with the new peptides, the structures of which are not yet elucidated.

The new peptides according to the invention, furthermore their salts and complexes can be converted into pharmaceutical compositions for enteral or parenteral administraiton. These compositions may contain, beside the active agent, organic or mineral carriers, diluents and/or auxiliary agents applicable in the pharmaceutical industry. The pharmaceutical compositions may be e.g. solid, freeze-dried substances containing a compound nonreacting with the peptide (such as a carbohydrate) as carrier, or concentrated or dilute suspensions or emulsions, which may also contain inert preservatives and/or stabilizing agents.

The pharmaceutical compositions according to the invention can be applied as diagnostic agents in the determination of the maximum gastric acid secretion. They can also be used in therapy of patients with decreased or no gastric acid secretion. The new compositions can be used to advantage in the treatment of praeatrophic gastritis and subacide complaints. Since pentagastrin exerts a trophic effect favoring the recovery of mucous membrane, the new compositions can also be used to advantage in the treatment of disorders connected with atrophic processes of the mucous membrane of the stomach.

The invention is elucidated in detail by the aid of the following non-limiting Examples. The abbreviations used in the Examples correspond to those used in the literature (J. Biol. Chem. 247, 977 [1972]). Further abbreviations are as follows:

OGly: α-(aminooxy)-acetic acid
OAla: α-(aminooxy)-propionic acid
DCC: dicyclohexyl carbodiimide
PCPOH: pentachlorophenol
PFPOH: pentafluorophenol
SuOH: N-hydroxy-succinimide
DMF: dimethyl formamide
HMFA: hexamethylphosphoric acid triamide The melting points were determined on a Dr. Tottoli type (Buchi) apparatus. The thin layer chromatograms were prepared on silica gel layers (Kieselgel G) prepared according to Stahl, and the following solvent mixtures were employed as eluting agents:
1. chaloroform : methanol : 95:5
2. chloroform - methanol : 9:1
3. chloroform : n-hexane : acetic acid : 8:1:1
4. ethyl acetate : P-AA-W : 9:1
5. ethyl acetate : P-AA-W : 8:2
6. ethyl acetate : P-AA-W : 7:3
7. ethyl acetate : P-AA-W : 3:2
8. ethyl acetate : P-AA-W: 1:1
9. ethyl acetate: P-AA-W : 2:3
10. ethyl acetate : P-AA-W : 85:15

The symbol P-AA-W represents a 20:6:11 mixture of pyridine, acetic acid and water.

The thin layer chromatograms were developed with ninhydrin solution. The chromatographic sheets were sprayed with ninhydrin solution, dried at 105° C. for about 5 minutes, subjected to chlorine gas, vented, and finally treated with o-toluidine-potassium iodide solution.

The column chromatographic purification of the substances was performed with silica gel (Kieselgel G), particle size: 62–200 μm.

EXAMPLE 1

Step 1

N-(Benzyloxycarbonyl)-L-phenylalanine-amide 12.0 g (40 mmoles) of Z—Phe—OH are dissolved in 80 ml of dry tetrahydrofuran, and 5.60 ml (40 mmoles) of triethylamine are added to the solution. The solution is cooled to −10° C., and 3.80 ml (40 mmoles) of ethyl chloroformate are added dropwise. The resulting suspension is stirred at −10° C. for 10 minutes, thereafter gaseous ammonia is introduced into the mixture for one hour. During this operation the mixture is cooled with water. Next day the reaction mixture is evaporated in vacuo, and the crystalline residue is triturated with 40 ml of warm (40–50° C.) water. The crude product, weighing 8.84 g, is recrystallized from a sevenfold amount of ethanol with decolourizing. 6.55 g (55%) of Z—Phe—NH$_2$ are obtained; m.p.: 165–166° C., R$_f^4$: 0.75.

Step 2

L-Phenylalanine-amide hydrobromide 6.55 g (22 mmoles) of Z—Phe—NH$_2$, prepared as described in Example 1, Step 1, are dissolved in 13 ml of acetic acid, and 30 ml of 5 n hydrogen bromide in acetic acid are added to the solution. After 5 minutes of stirring a thick precipitate separates. The suspension is allowed to stand for one hour, thereafter it is diluted with dry ether and filtered. The crude product is dissolved in 240 ml of ethanol, the solution is decolorized, and the product is precipitated with 740 ml of ether. 4.90 g (91%) of H—Phe—NH$_2$.HBr are obtained; the white, crystalline substance is chromatographically uniform. (Two spots appear on the thin layer chromatogram: one of them belongs to the product and the other to hydrogen bromide). M.P.: 249–250° C., R$_f^8$: 0.50; R$_f^8$,HBr: 0.35.

Step 3

N-(Benzyloxycarbonyl)-L-aspartyl-β-(tert.-butyl ester)-L-phenylalanine-amide 9.45 g (38.5 mmoles) of H—Phe—NH$_2$.HBr, prepared as described in Example 1, Step 2, are treated with 5.40 ml (38.5 mmoles) of triethylamine in 100 ml of dry tetrahydrofuran in order to liberate the base. 16.2 g (38.5 mmoles) of Z—Asp(O$^t$Bu)-OSu are added to the suspension. Next day the reaction mixture is evaporated in vacuo, the residue is dissolved in 500 ml of ethyl acetate, and the solution is washed thrice with 10% citric acid solution and thrice with 5% sodium bicarbonate solution. The solution is decolorized with charcoal under heating, filtered, dried over sodium sulfate, filtered again, and concentrated in vacuo. The separated substance is dissolved in about 200 ml of the same solvent, and then the end-product is allowed to crystallize. 15.17 g (84%) of Z—Asp (O$^t$Bu)—Phe—NH$_2$ are obtained; the chromatographically uniform substance melts at 160–161° C. R$_f^4$: 0.70.

Step 4

L-Aspartyl-β-(tert.-butyl ester)-L-phenylalanine-amide 2.0 g of palladium-on-carbon catalyst are added to a solution of 15.17 g (32.3 mmoles) of Z—Asp(O$^t$Bu)—Phe—NH$_2$, prepared as described in Example 1, Step 3, in 1.0 l of methanol, and gaseous hydrogen is bubbled through the stirred mixture. After 2 hours the suspension is filtered, the filtrate is evaporated in vacuo, the solid residue is triturated with diisopropyl ether, and the suspension is allowed to stand at a cold place overnight. The separated substance is filtered off. 10.40 g (95.8%) of H—Asp(O$^t$Bu)—Phe—Nh$_2$ are obtained; m.p.: 121.0–121.5° C., R$_f^4$: 0.35.

Step 5

N-(tert.-Butoxycarbonyl)-L-methionyl-L-aspartyl-β-(tert.-butyl-ester)-L-phenylalanine-amide 10.4 g (31 mmoles) of H—Asp(O$^t$Bu)—Phe—NH$_2$, prepared as described in Example 1, Step 4, and 11.1 g (32 mmoles) of BOC—Met—OSu are dissolved in 100 ml of chloroform, and the solution is allowed to stand overnight. Next day the reaction mixture is washed thrice with water, the chloroform solution is dried, and evaporated in vacuo. The gelly residue is triturated with ether, the mixture is allowed to stand at a cool place, and the precipitate is filtered off. 14.5 g (82.7%) of crude product are obtained; m.p.: 148–149° C. The crude product is dissolved in 40 ml of methanol, the solution is decolorized with charcoal, filtered, and the filtrate is diluted with 40 ml of ether. 12.80 g (73%) of BOC—Met—Asp(O$^t$Bu)-Phe—NH$_2$ are obtained; m.p.: 151–152° C., R$_f^4$: 0.65.

Step 6

L-Methionyl-L-aspartyl-L-phenylalanine-amide hydrochloride 12.50 g (22.1 mmoles) of BOC—Met—Asp(O$^t$Bu)—Phe—NH$_2$, prepared as described in Example 1, Step 5, are dissolved in 25 ml of warm acetic acid, the solution is cooled, and 30 ml of 7.4 n hydrochloric acid in ethyl acetate are added. After 5 minutes the reaction mixture turns turbid and an oil separates. After 10 minutes the mixture is diluted with ether and the resulting suspension is filtered. The obtained crude product, weighing 10.24 g (over 100%), is dissolved in 40 ml of methanol, and 200 ml of ethyl acetate are added to precipitate the product. A gel substance separates, which is difficult to filtrate. The mixture is allowed to stand at a cold place overnight, and then it is filtered. 9.0 g (91 %) of H—Met—Asp—Phe—NH$_2$.HCl are obtained; m.p.: 187–189° C., R$_f^6$: 0.27.

Step 7

N-(tert.-Butoxycarbonyl)-L-tryptophyl-L-methionyl-L-aspartyl-L-phenylalanine-amide 9.0 g (20.1 mmoles) of H—Met—Asp—Phe—NH$_2$.HCl, prepared as described in Example 1, Step 6, and 8.42 g (21 mmoles) of BOC—Trp—OSu are suspended in 150 ml of dimethyl formamide, and 2.83 ml (20.1 mmoles) of triethylamine are added to the suspension. The reaction mixture is stirred overnight, and then poured onto a mixture of 1.0 l of ice water and 3.75 ml of acetic acid. The suspension is allowed to stand until the ice melts, and then it is filtered. The gelly precipitate is washed with water and then with a great proportion of ether. The resulting crude product, weighing 13.3 g (95 %) (m.p.: 203–204° C.), is recrystallized twice from about 30-fold 80% aqueous ethanol. 9.67 g (69%) of BOC—Trp—Met—Asp—Phe—NH$_2$ are obtained; m.p.: 212–214° C. (decomposition), R$_f^5$: 0.43.

Step 8

L-Tryptophyl-L-methionyl-L-aspartyl-L-phenylalanine-amide monohydrate 9.23 g (13.2 mmoles) of BOC—Trp—Met—Asp—Phe—NH$_2$, prepared as described in Example 1, Step 7, are poured into a stirred mixture of 32 ml of trifluoroacetic acid, 8 ml of water and 4 ml of anisol at 0° C. Nitrogen is bubbled through the mixture for 2 hours, and then the solution is diluted with 270 ml of ether under cooling. The resulting suspension is filtered, the precipitate is washed with a great proportion of ether, and dried in a desiccator. The crude product is dissolved in 60 ml of methanol, and the trifluoroacetate is precipitated with 240 ml of ether. The purified salt is dissolved in a mixture of 340 ml of water and 29 ml of 1 n sodium hydroxide solution, and the free tetrapeptide-amide is precipitated with 13.2 ml of acetic acid. The suspension is allowed to stand at a cold place for a short time, then the precipitate is filtered off and washed with a great proportion of water. 6.70 g (82.4%) of H—Trp—Met—Asp—Phe—NH$_2$.H$_2$O are obtained; m.p.: 235–238° C., R$_f^6$: 0.35.

Analysis: Calculated for C$_{29}$H$_{36}$O$_6$N$_6$S.H$_2$O (M.wt.: 614.725): C: 56.6%, H: 6.2%, N: 13.7%. Found: C: 56.4%, H: 6.2%, N: 13.6%.

Step 9 tert.-Butoxycarbonyl-aminooxy-acetic acid pentachlorophenyl ester 8.0 g (41.8 mmoles) of BOC—OGly—OH and 11.1 g (42.0 mmoles) of pentachlorophenol are dissolved in 160 ml of dry dioxane. The solution is cooled below 5° C., and 8.6 g (42.0 mmoles) of dicyclohexyl carbodiimide are added. The reaction mixture is allowed to stand at room temperature overnight, and then the separated dicyclohexyl urea (DCU) is filtered off. The filtrate is evaporated in vacuo and the solid residue is recrystallized from a mixture of dioxane and ethanol. 13.7 g (74.3%) of BOC—OGly-OPCP are obtained; m.p.: 167°–168° C., R$_f^3$: 0.7.

Analysis: Calculated for C$_{13}$H$_{12}$O$_5$NCl$_5$ (M.wt.: 439.51): C: 35.52%, H: 2.75%, N: 3.18%, Cl: 40.33%. Found: C: 35.37%, H: 2.90%, N: 3.31%, Cl: 40.12%.

Step 10

(tert.-Butoxycarbonyl-aminooxy)-acetyl-L-tryptophyl-L-methionyl-L-aspartyl-L-phenylalanine-amide 1.79 g (3.0 mmoles) of H—Trp—Met—Asp—Phe—NH$_2$.H$_2$O, prepared as described in Example 1, Step 8, are reacted with 1.18 g (3.3 mmoles) of BOC—OGly—OPCP, prepared as described in Example 1, Step 9, in 30 ml of dimethyl formamide. After 4 hours the reaction mixture is evaporated in vacuo and the gelly residue is triturated with ethyl acetate. The crude product, weighing 2.11 g (91%) and melting at 178°–184° C. under decomposition, is dissolved in 20 ml of methanol, the solution is decolourized, and the product is precipitated with water. 1.50 g (64.8%) of white, crystalline BOC—OGly—Trp—Met—Asp—Phe—NH$_2$ are obtained; m.p.: 193°–194° C., R$_f^5$: 0.40, [α]$_D$: −16.2° (c: 1.0, in dimethyl formamide).

Analysis: Calculated for C$_{36}$H$_{47}$O$_{10}$N$_7$S (M.wt.: 769.85): C: 56.1%, H: 6.1%, S: 4.16%. Found: C: 56.4%, H: 6.3%, S: 4.07%.

EXAMPLE 2

(Aminooxy)-acetyl-L-tryptophyl-L-methionyl-L-aspartyl-L-phenylalanine-amide 1.0 g (1.3 mmoles) of BOC—OGly—Trp—Met—Asp—Phe—NH$_2$, prepared as described in Example 1, Step 10, is poured into a stirred mixture of 4 ml of trifluoroacetic acid, 1 ml of water and 0.5 ml of anisol, and nitrogen is bubbled through the mixture for 2 hours. The reaction mixture is diluted with 40 ml of ether, and the trifluoroacetate salt is separated. 1.02 g of the salt are dissolved in a mixture of 34 ml of water and 2.9 ml of 1 n sodium hydroxide solution, and the free amide is precipitated by adding 1.32 ml of acetic acid to the mixture. The precipitate is filtered off, washed thoroughly with water, and dried in a desiccator. 0.6 g (69%) of H—OGly—Trp—Met—Asp—Phe—NH$_2$ are obtained; m.p.: 183°–184° C., R$_f^6$: 0.5, [α]$_D$: −31.6° (c: 1.0, in dimethyl formamide).

Analysis: Calculated for $C_{31}H_{39}O_8N_7S$ (M.wt.: 669.763): C: 55.59%, H: 5.87%, N: 14.60%, S: 4.79%. Found: C: 55.41%, H: 5.93%, N: 14.41%, S: 4.71%.

EXAMPLE 3

Step 1

2-(tert.-Butoxycarbonyl-aminooxy)-L-propionic acid pentachlorophenyl ester 4.10 g (20 mmoles) of BOC—D—OAla and 5.32 g (20 mmoles) of pentachlorophenol are dissolved in 20 ml of dimethyl formamide, the solution is cooled to 0° C., and 4.12 g (20 mmoles) of DCC are added. The reaction mixture is stirred for 30 minutes at 0° C. and then allowed to stand at room temperature overnight. The separated DCU is filtered off, the filtrate is evaporated in vacuo, and the crystalline residue is triturated with dry ether. The crude product, weighing 6.25 g, is filtered off and crystallized from ethanol. 5.80 g (63%) of BOC—D—OAla—OPCP are obtained; m.p.: 122°–124° C., $R_f^3$: 0.85, $[\alpha]_D$: −68.87° (c: 1.0, in dioxane).

Analysis: Calculated for $C_{14}H_{14}O_5NCl_5$ (M.wt.: 453.537): C: 37.07%, H: 3.11%, Cl: 39.08%. Found: C: 37.22%, H: 3.07%, Cl: 39.27%.

Step 2

2-(tert.-Butoxycarbonyl-aminooxy)-L-propionyl-L-tryptophyl-L-methionyl-L-aspartyl-L-phenylalanine-amide 0.70 g (1.22 mmoles) of H—Trp—Met—Asp—Phe—NH$_2$.H$_2$O, prepared as described in Example 1, Step 8, are reacted with 0.59 g (1.30 mmoles) of BOC—L—OAla—OPCP, prepared as described in Example 3, Step 1, in 50 ml of dimethyl formamide in the presence of 0.35 ml (2.5 mmoles) of triethylamine. Next day the reaction mixture is evaporated in vacuo, the gelly residue is triturated with ethyl acetate, and filtered. The resulting crude product, weighing 0.69 g, is admixed with 15 ml of ethyl acetate, the mixture is heated to boiling, and the suspension is filtered when hot. The purified substance, weighing 0.50 g, is dissolved in a small amount of solvent mixture 6, the solution is poured onto a column filled with 40 g of silica gel, and the column is eluted with solvent mixture 5. 0.30 g of chromatographically uniform BOC—L—OAla—Trp—Met—Asp—Phe—NH$_2$ are separated from the pure fractions; m.p.: 199° C. (decomposition), $R_f^4$: 0.15, $R_f^5$: 0.30.

Analysis: Calculated for $C_{37}H_{49}O_{10}N_7S$ (M.wt.: 783.88): C: 56.69%, H: 6.30%, N: 12.51%. Found: C: 56.50%, H: 6.29%, N: 12.34%.

EXAMPLE 4

Step 1

N-(Benzyloxycarbonyl)-L-leucyl-L-aspartyl-β-(tert.-butyl ester)-L-phenylalanine-amide 5.0 g (14.9 mmoles) of H—Asp(O$^t$Bu)—Phe—NH$_2$, prepared as described in Example 1, Step 4, are reacted with 5.5 g (15.2 mmoles) of Z—Leu—OSu in 50 ml of chloroform. The initially clear reaction mixture gellifies with the progress of the reaction, and then it solidifies. The mixture is diluted with chloroform, stirred overnight, and then evaporated in vacuo. The residue is triturated with water and filtered. The crude product, weighing 8.6 g and melting at 170° C., is crystallized from 45 ml of ethanol. 7.26 g (83.5%) of Z—Leu—Asp-(O$^t$Bu)—Phe—NH$_2$ are obtained; m.p.: 180°–181° C., $R_f^4$: 0.6, $[\alpha]_D$: −36.8° (c: 1.0, in ethanol).

Analysis: Calculated for $C_{31}H_{42}O_7N_4$ (M.wt.: 582.68): C: 63.90%, H: 7.27%, N: 9.62%. Found: C: 63.70%, H: 7.41%, N: 9.73%.

Step 2

L-Leucyl-L-aspartyl-β-(tert.-butyl ester)-L-phenylalanine-amide 6.76 g (11.6 mmoles) of Z—Leu—Asp(O$^t$Bu)—Phe—NH$_2$, prepared as described in Example 4, Step 1, are dissolved in 300 ml of methanol. 1.0 g of palladium-on-carbon is added to the solution, and hydrogen is bubbled through the stirred mixture. After 1.5 hours the catalyst is filtered off, and the filtrate is evaporated. The gel residue is triturated with n-hexane. The resulting 5.2 g (99.5%) of H—Leu—Asp(O$^t$Bu)—Phe—NH$_2$ ($R_f^4$: 0.1) is used in the next step without further purification.

Step 3

N-(tert.-Butoxycarbonyl)-L-tryptophyl-L-leucyl-L-aspartyl-β-(tert.-butyl ester)-L-phenylalanine-amide 5.2 g (11.5 mmoles) of H—Leu—Asp(O$^t$Bu)—Phe—NH$_2$, prepared as described in Example 4, Step 2, and 4.82 g (12.0 mmoles) of BOC—Trp—OSu are dissolved in 100 ml of DMF, and the solution is allowed to stand. Next day the reaction mixture is evaporated in vacuo, the solid residue is triturated with water, and filtered. The crude product, weighing 8.95 g (over 100%) is recrystallized from 70 ml of 70% ethanol with decolourizing. 7.19 g (84.5%) of BOC—Trp—Leu—Asp(O$^t$Bu)—Phe—NH$_2$ are obtained; m.p.: 176°–177° C., $R_f^4$: 0.65. A sample of the product is recrystallized from a tenfold amount of 80% ethanol. The analytical sample melts at 180°–182° C., $[\alpha]_D$: −35.3° (c: 1.0, in dimethyl formamide).

Analysis: Calculated: C: 63.74%, N: 7.41%, N: 11.47%. Found: C: 63.62%, H: 7.62%, N: 11.17%.

Step 4

L-Tryptophyl-L-leucyl-L-aspartyl-L-phenylalanine-amide 6.59 g (9.0 mmoles) of BOC—Trp—Leu—Asp(O$^t$Bu)—Phe—NH$_2$, prepared as described in Example 4, Step 3, are poured into a mixture of 60 ml of trifluoroacetic acid and 6 ml of anisol. The reaction mixture is stirred at room temperature for 2 hours and then diluted with dry ether. The pasty substance is filtered off and dried in a desiccator over sodium hydroxide and phosphorous pentoxide. The crude product is triturated with water to obtain 5.61 g of the trifluoroacetate; m.p.: 178°–186° C. (decomposition). The salt is dissolved in warm water containing a small amount of ethanol, and the pH of the solution is adjusted to 7 with 1 n sodium hydroxide solution under cooling. The separated precipitate is filtered off and washed with water and ethanol. The crude product, weighing 4.0 g, is washed first with ethanol, then dissolved in 30 ml of DMF, and precipitated with 60 ml of ethanol. 2.28 g of H—Trp—Leu—Asp—Phe—NH$_2$ are obtained; the chromatographically uniform product melts at 227°–230° C. (decomposition), $R_f^6$: 0.55.

Analysis: Calculated for $C_{30}H_{38}N_6O_6$ (M.wt.: 578.67): C: 62.26%, H: 6.62%, N: 14.52%. Found: C: 62.02%, H: 6.80%, N: 14.38%.

Step 5

2-(tert.-Butoxycarbonyl-aminooxy)-acetyl-L-tryptophyl-L-leucyl-L-aspartyl-L-phenylalanine-amide 1.0 g (1.82 mmoles) of H—Trp—Leu—Asp—Phe—$NH_2$, prepared as described in Example 4, Step 4, and 0.88 g (2.0 mmoles) of BOC—OGly—OPCP are dissolved in 10 ml of DMF, and 0.27 ml (1.82 mmoles) of triethylamine are added to the solution. Next day the reaction mixture is evaporated in vacuo, the residue is triturated with ether, the resulting suspension is allowed to stand at a cold place, and then filtered. The obtained crude product, weighing 1.42 g and melting at 102°–120° C. under decomposition, is admixed with a tenfold amount of ethyl acetate, the mixture is boiled, and the suspension is filtered when hot. The resulting substance, weighing 1.06 g, is dissolved in solvent mixture 5, the solution is poured onto a column filled with 80 g of silica gel, and the column is eluted with solvent mixture 10. The pure fractions are combined. 0.58 g of BOC—OGly—Trp—Leu—Asp—Phe—$NH_2$ are obtained; m.p.: 187° C. (decomposition). $[\alpha]_D$: $-24.9°$ (c: 0.5, in dimethyl formamide), $R_f^6$: 0.7, $R_f^4$: 0.15.

Analysis: Calculated for $C_{37}H_{49}O_{10}N_7$ (M.wt.: 751.85): C: 59.11 %, H: 6.57 %, N: 13.04 %. Found: C: 59.28 %, H: 6.40 %, N: 12.75 %.

EXAMPLE 5

Step 1

L-Leucyl-L-aspartyl-L-phenylalanine-amide hydrochloride 6.19 g (15.4 mmoles) of H—Leu—Asp(O'Bu)—Phe—$NH_2$, prepared as described in Example 4, Step 2, are poured into 50 ml of acetic acid containing hydrochloric acid. After 45 minutes the solution is diluted with dry ether, the suspension is allowed to stand at a cold place for a short time, and then filtered. The precipitate is washed thoroughly with dry ether. 6.20 g (94 %) of H—Leu—ASp—Phe—$NH_2$.HCl ($R_f^6$: 0.2) are obtained. The substance is used without further purification in the next step.

Step 2

N-(tert.-Butoxycarbonyl)-L-tryptophyl-L-leucyl-L-aspartyl-L-phenylalanine-amine 6.2 (14.5 mmoles) of H—Leu—Asp—Phe—$NH_2$.HCl, prepared as described in Example 5, Step 1, are reacted with 6.42 g (16.0 mmoles) of BOC—Trp—OSu in 70 ml of DMF in the presence of 2.24 ml (16.0 mmoles) of trimethylamine. After 4 hours the reaction mixture is evaporated in acuo, the residue is triturated with water and filtered. The crude product, weighing 10.6 g, is boiled twice in a mixture of methanol and ethyl acetate, the gel product is allowed to stand at a cold place, and then filtered. 7.1 g (72.1 %) of BOC—Trp—Leu—Asp—Phe—$NH_2$ are obtained; m.p.: 218°–221° C. (decomposition), $R_f^5$: 0.4. This substance is used in the next step without further purification.

Step 3

L-Tryptophyl-L-leucyl-L-aspartyl-L-phenylalanine-amide 7.1 g (10.5 mmoles) of BOC—Trp—Leu—Asp—Phe—$NH_2$, prepared as described in Example 5, Step 2, are poured into 60 ml of hydrochloric acid in dioxane. The reaction mixture is initially turbid, but it gets clear within 3 minutes. After 10 minutes the solution is diluted with dry ether, the separated oily substance is solidified and filtered off. The resulting 6.96 g of hydrochloride are dissolved in 150 ml of warm water. Te pH of the solution is adjusted to 7 with solid sodium bicarbonate under cooling. The resulting suspension is filtered, and the precipitate is washed with a great proportion of water. 5.05 g (83.1 %) of H—Trp—Leu—Asp—Phe—$NH_2$ are obtained; the chromatographically uniform substance melts at 228°–230° C. (decomposition). The product is identical with that obtained in Example 4, Step 4.

Step 4

2-(tert.-Butoxycarbonyl-aminoxy)-D-propionic acid pentachlorophenyl ester 4.10 g (20 mmoles) of BOC—D—OAla—OH and 5.32 g (20 mmoles) of pentachlorophenol are dissolved in 20 ml of dimethyl formamide, the solution is cooled to 0° C., and 4.12 g (20 mmoles) of DCC are added. The reaction mixture is stirred for 0.5 hours at 0° C. and then allowed to stand at room temperature overnight. The separated DCU is filtered off, the filtrate is evaporated in vacuo, and the crystalline residue is triturated with ether. The resulting crude product, weighing 6.25 g, is crystallized from ethanol. 5.80 g (64 %) of BOC—D—OAla—OPCP are obtained; m.p.: 123°–124° C., $R_f^3$: 0.85, $[\alpha]_D$: $+68.95°$ (c: 1.0, in dioxane).

Analysis: Calculated for $C_{14}H_{14}O_5NCl_5$ (M.wt.: 453.537): C: 37.10 %, H: 3.10 %, Cl: 39.10 %. Found: C: 37.16 %, H: 3.29 %, Cl: 39.01 %.

Step 5

2-D-(tert.-Butoxycarbonyl-aminooxy)-propionyl-L-tryptophyl-L-leucyl-L-aspartyl-L-phenylalanine-amide 1.74 g (3.0 mmoles) of H—Trp—Leu—Asp—Phe—$NH_2$, prepared as described in Example 4, Step 4 or Example 5, Step 3, and 1.50 g (3.3 mmoles) of BOC—D—OAla—OPCP, prepareed as described in Example 5, Step 4, are reacted in 20 ml of DMF in the presence of 0.42 ml (3.0 mmoles) of triethylamine. Next day the reaction mixture is evaporated in vacuo and the residue is triturated with ether. The obtained crude product, weighing 2.61 g (over 100%), is dissolved in a small amount of solvent mixture 5, the solution is poured onto a column filled with 100 g of silica gel, and eluted with solvent mixture 5. The pure fractions are pooled, and th crystalline residue is recrystallized from 50 ml of 80% ethanol. 1.07 g (46.7%) of BOC—D—OAla—Trp—Leu—Asp—Phe—$NH_2$ are obtained; the substance decomposes at 210° C. $[\alpha]_D$: $-6.0°$ (c: 1, in dimethyl formamide), $R_f^4$: 0.15, $R_f^5$: 0.40.

Analysis: Calculated fo $C_{38}H_{51}O_{10}N_7$ (M.wt.: 765.88): C: 59.95%, H: 6.71%, N: 12.80%. Found: C: 59:37%, H: 6.90% N: 13.10%.

EXAMPLE 6

Step 1

2-(N-(tert.-Butoxycarbonyl)-L-phenylalanyl-aminooxy)-acetic acid 6.97 g (40.5 mmoles) of aminooxy-acetic acid hydrobromide are reacted with 14.68 g (40.5 mmoles) of BOC—Phe—OSu in 100 ml of DMF in the presence of 6.3 ml (45 mmoles) of triethylamine. Next day the reaction mixture is evaporated in vacuo, the oily residue is dissolved in 100 ml of chloroform, and the chloroform solution is washed thrice with 1 n hydrochloric acid. The organic solution is dried, evaporated in vacuo, and the oily residue is solidified with diisopropyl ether. The crude product is purified by precipitation from an ethyl acetate-diisopropyl ether solvent system. 9.70 g (74%) of BOC—Phe—OGly—OH are obtained; m.p.: 136°-137° C., $R_f^5$: 0.4, $[\alpha]_D$: −17.8° (c: 1.0, in ethanol).

Analysis: Calculated for $C_{16}H_{22}O_6N_2$ (M.wt.: 338.36): C: 56.80%, H: 6.55%, N: 8.28%. Found: C: 56.59%; H: 6.41%, N: 8.42%.

Step 2

N-(tert.-Butoxycarbonyl)-L-aspartyl-β-(tert.-butylester)-α-(N-hydroxy-succinimido-ester)

18.8 g (40 mmoles) of BOC—Asp(O$^t$Bu)—OH.DCHA are partitioned between 240 ml of ether and 240 ml of water containing 1.2 ml of concentrated sulfuric acid. The etheral phase is washed with a solution of 0.4 ml of concentrated sulfuric acid in 80 ml of water and then with water. The etheral solution is dried and evaporated in vacuo.

The resulting 11.45 g (39.7 mmoles) of oily BOC—Asp(O$^t$Bu)—OH and 4.6 g (40 mmoles) of N-hydroxy-succinimide are dissolved in 100 ml of dry dioxane. The solution is cooled until freezing, and then 8.25 g (40 mmoles) of DCC are added. The reaction mixture is stirred at room temperature overnight, the separated DCU is filtered off, and the filtrate is evaporated. The oily residue is solidified with a mixture of n-hexane and diisopropyl ether. The resulting crude product, weighing 13.8 and melting at 98°-102° C., is recrystallized from a threefold amount of isopropanol. 12.1 g (78.3%) of white, crystalline BOC—Asp (O$^t$Bu)—OSu are obtained; m.p.: 103°-105° C., $[\alpha]_D$: −25.6° (c: 1.0, in dioxane).

Analysis: Calculated for $C_{17}H_{26}O_8N_2$ (M.wt.: 386.39): C: 52.84% H: 6.78%, N: 7.25%. Found: C: 52.97%, H: 6.90%, N: 7.21%.

Step 3

2-(L-Phenylalanyl-aminooxy)-acetic acid hydrochloride 5.8 g (17.1 mmoles) of BOC—Phe—OGly—OH, prepared as described in Example 6, Step 1, are dissolved in 10 ml of ethyl acetate, and 60 ml of 4 n hydrochloric acid in ethyl acetate are poured into the solution. The mixture is stirred for one hour, thereafter the solvent is decanted from the oily product, and the product is solidified with fresh ethyl acetate. 4.53 g (96.6%) of H—Phe—OGly—OH.HCl are obtained; m.p.: 75°-80° C., $R_f^8$: 0.2(the product is chromatographically uniform). Owing to its hygroscopic nature, the product can be stored only in a desciccator.

Step 4

2-(N-(tert.-Butoxycarbonyl)-L-aspartyl-β-)tert.-butylester)-L-phenylalanyl-aminooxy)-acetic acid 7.0 g (25.5 mmoles) of H—Phe—OGly—OH.HCl, prepared as described in Example 6, Step 3, are dissolved in 150 ml of DMF, and 7.15 ml (51 mmoles) of triethylamine are added to the solution. 9.30 g (24 mmoles) of BOC—Asp(O$^t$Bu)—OSu, prepared as described in Example 6, Step 2, are poured into the resulting suspension, and the solids are allowed to dissolve; The reaction mixture is allowed to stand overnight. Thereafter the mixture is evaporated in vacuo, the oily residue is dissolved in 150 ml of chloroform, the chloroform solution is washed thrice with 1 n hydrochloric acid and water, dried, and evaporated in vacuo. The residue is solidified by treating it with diisopropyl ether, and the resulting crude product, weighing 10.35 g, is precipitated twice from a mixture of ether and n-hexane. 8.63 g (70.7) of BOC—Asp(O$^t$Bu)—Phe—OGly—OH are obtained: m.p.: 83°-85° C. (decomposition), $[\alpha]_D$: −30.6° (c=1.36, in ethanol), $R_f^5$=0.45. Based on chromatographic examination, the substance contains a small amount of impurity.

Step 5

2-(L-Aspartyl-L-phenylalanyl-aminooxy)-acetic acid hydrochloride 8.50 g (16.7 mmoles) of BOC—Asp(O$^t$Bu)—Phe—OGly—OH, prepared as described in Example 6, Step 4, are poured into 70 ml (350 mmoles) of 5 n hydrochloric acid in ethyl acetate under stirring. The starting substance dissolved immediately, and the end-product starts to separate from the mixture as a crystalline substance after 5 minutes. After 75 minutes the suspension is filtered and the precipitate is washed with ethyl acetate. 6.22 g (95.8%) of crystalline H—Asp—Phe—OGly—OH.HCl are obtained; m.p.: 160°-163° C., $R_f^9$=0.25.

Step 6

2-(N-(tert.-Butoxycarbonyl)-L-methionyl-L-aspartyl-L-phenylalanyl-aminooxy)acetic acid 6.1 g (15.6 mmoles) of H—Asp—Phe—OGly—OH.HCl, prepared as described in Example 6, Step 5, are dissolved in 50 ml of DMF, 6.55 ml (46.8 mmoles) of triethylamine are added to the solution, and then 6.38 g (15.6 mmoles) of BOC—Met—OSu are dissolved in the resulting suspension. The reaction mixture is allowed to stand at room temperature overnight, and then it is evaporated in vacuo. The oily residue is solidified with diisopropyl ether and the crude product, weighing 6.3 g (69%), is isolated by filtration. The crude substance is dissolved in a small amount of solvent mixture 7, and the solution is poured onto a column filled with 110 g of silica gel. The column is eluted with the solvent mixture 7 at a rate of 8 to 10 ml/hour. The pure fractions are pooled, evaporated in vacuo, and the oily residue is solidified with diisopropyl ether. The resulting product, weighing 4.4 g, is dissolved in 15 ml of methanol and precipitated with a tenfold amount of dry ether. 3.26 g (35.7%) of amorphous, chromatographically uniform BOC—Met—Asp—Phe—OGly—OH are obtained; $R_f^7$=0.30, $[\alpha]_D$: −37.2° (c=1.0, in ethanol).

Analysis: Calculated for $C_{25}H_{36}O_{10}N_4S$ (M.wt.: 584.65): C: 51.36%, H: 6.21%, N: 9.58%, S: 5.48%. Found: C: 51.50%, H: 6.07%, N: 9.43%, S: 5.47%.

Step 7

2-(L-Methionyl-L-aspartyl-L-phenylalanyl-aminooxy)-acetic acid hydrochoride 0.50 g (0.85 mmoles) of BOC—Met—Asp—Phe—OGly—OH, prepared as describedin Example 6, Step 6, are treated for 1 hour with 5 ml of hydrochloric acid in ethyl acetate. The suspension is filtered, the precipitate is washed thoroughly with ethyl acetate, and dried in a desiccator. 0.41 g (91%) of amorphous H—Met—Asp—Phe—OGly—OH.HCl are obtained; $R_f^7$=0.05, $R_f{}^8=0.2$. Based on chromatographical examination, the substance contains a small amount of impurities.

Step 8

2-(N-tert.-Butoxycarbonyl)-L-tryptophyl-L-methionyl-L-aspartyl-L-phenylalanyl-aminooxy)-acetic acid 3.0 g (4.79 mmoles) of H—Met—Asp—Phe—O—Gly—OH.HCl, prepared as described in Example 6, Step 7, are suspended in 50 ml of DMF, and 1.4 ml (10 mmoles) of triethylamine and 2.35 g (5.0 mmoles) of BOC—Trp—OPFP are added to the stirred mixture. After 1.5 hours the reaction mixture is evaporated in vacuo, the residue is dissolved in ethyl acetate, and the solution is washed thrice with 1 n hydrochloric acid and then with water. The ethyl acetate solution is dried, decolourized, and evaporated in vacuo to a final volume of 10 ml. Dry ether is added to this concentrate to precipitate the end-product. The suspension is allowed to stand at a cool place and then filtered. The crude product, weighing 3.04 g, is dissolved in 5 ml of ethanol and precipitated with 200 ml of ether. 2.17 g (58.8%) of amorphous BOC—Trp—Met—Asp—Phe—O—Gly—OH are obtained; $R_f{}^7=0.3$, $[\alpha]_D$: $-19.9°$ (c=0.75, in dimethyl formamide). On the basis of chromatographic examination the substance is slightly impure.

Step 9

2-(L-Tryptophyl-L-methionyl-L-aspartyl-L-phenylalanyl-aminooxy)-acetic acid 2.17 g (2.81 mmoles) of BOC—Trp—Met—Asp—Phe—OGly—OH, prepared as described in Example 6, Step 8, are poured into a stirred mixture of 8 ml of trifluoroacetic acid, 2 ml of water and 1 ml of anisol, and nitrogen is bubbled through the mixture for 2 hours. The solution is diluted with 60 ml of ether, the separated product is filtered off and dried in a desiccator. The resulting 2.0 g of trifluoroacetate are dissolved in 8 ml of 2 n sodium hydroxide solution, and the pH of the solution is adjusted to 4 with 10% aqueous hydrochloric acid. The separated precipitate is filtered off and washed with water. 1.34 g (71%) of amorphous H—Trp—Met—Asp—Phe—OGly—OH are obtained, $R_f{}^7=0.1$. The product, which contains a small amount of impurities on the basis of chromatography, is used in the next reaction without purification.

Step 10

3-Bromopropionic acid 44.0 g (0.49 mmoles) of β-alanine and 200 g (1.68 mmoles) of KBr are dissolved in 1.0 l of 2.5 n sulfuric acid, and 42.4 g (0.76 moles) of sodium nitrite are added in portions to the mixture at room temperature. The reaction mixture is stirred for 2 hours at room temperature and then extracted with 2×200 ml of ether. The etheral solution is washed thrice with water, dried, and evaporated in vacuo. The resulting crude product, Weighing 19.8 g, is recrystallized from 30 ml of n-hexane with decolourizing. 18.1 g (24%) of 3-bromopropionic acid are obtained; m.p.: 59°–60° C.

Step 11

3-(tert.-Butoxycarbonyl-aminooxy)-propionic acid dicyclohexylammonium salt 7.7 g (0.30 moles) of metallic sodium are dissolved in 450 ml of ethanol, and a solution of 26.6 g (0.20 moles) of N-(tert.-butoxycarbonyl)-hydroxylamine in 165 ml of ethanol and a solution of 28.7 g (0.188 moles) of 3-bromopropionic acid, prepared as described in Example 6, Step 10, in 165 ml of ethanol are added to the sodium ethoxide solution. The reaction mixture is stirred at 50° to 55° C. for 2 days, evaporated in vacuo, and the residue is dissolved in 350 ml of water. The aqueous solution is washed with 3×100 ml of ethyl acetate, acidified to pH=3 with citric acid, saturated with sodium chloride, and extracted with 5×100 ml of ethyl acetate. The ethyl acetate solutions are combined, washed thrice with water, dried and evaporated in vacuo. 100 ml of n-hexane are layered onto the oily residue weighing 27.25 g, and 23.3 ml (118 mmoles) of dicyclohexylamine are aded to the cooled mixture in portions. The solid precipitate is allowed to stand at a cold place, thereafter it is filtered off and washed with ether. The crude product, weighing 44.93 g and melting at 128°–135° C., is dissolved in 50 ml of methanol, the solution is decolourized, and the end-product is precipitated with 200 ml of ether. 25.0 g (34%) of BOC—β—OAla—OH.DCHA are obtained; m.p.: 148°–149° C., $R_f{}^3=0.5$, $R_f{}^3{}_{salt}=0.25$.

From the mother liquor further 9.3 g (12.8%) of the product can be isolated; m.p.: 144°–145° C.

Analysis: Calculated for $C_{20}H_{38}O_5N_2$ (M.wt.: 386.52): C: 62.14%, H: 9.91%, N: 7.25%. Found: C: 61.99%, H: 10.02%, N: 7.09%.

Step 12

3-(tert.-Butoxycarbonyl-aminooxy)-propionic acid pentafluorophenyl ester 1.10 g (2.85 mmoles) of BOC—β—OAla—OH.DCHA, prepared as described in Example 6, Step 11, are partitioned between 40 ml of ether and 3 ml of 2 n sulfuric acid. The etheral phase is washed once again with aqueous sulfuric acid, then the sulfuric acid phases are combined and washed with ether. The etheral solutions are combined, dried and evaporated in vacuo. The resulting 0.34 g (1.66 mmoles) of oily substance and 0.31 g (1.8 mmoles) of pentafluorophenol are dissolved in 10 ml of dry dioxane, and 0.37 g (1.8 mmoles) of DCC are added to the solution at 5° C. The reaction mixture is stirred at room temperature for 1.5 hours, the separated DCU is filtered off, and the filtrate is evaporated in vacuo. The residue is dissolved in n-hexane, the solution is washed thrice with 5% aqueous sodium hydrocarbonate solution, dried, decolourized, and evaporated in vacuo. The oily residue is solidified with n-pentane. 0.33 g (55%, calculated for the acid) of BOC—β—OAla—OPFP are obtained; m.p.: 58°–59° C., $R_f{}^3=0.65$.

Analysis: Calculated for $C_{14}H_{14}O_5NF_5$ (M.wt.: 371.27): C: 45.29%, H: 3.80%, N: 3.77%. Found: C: 45.43%, H: 3.65%, N: 3.90%.

Step 13

2-(3-(tert.-Butoxycarbonyl-aminooxy)-propionyl-L-tryptophyl-L-methionyl-L-aspartyl-L-phenylalanyl-aminooxy)-acetic acid 0.32 g (0.48 mmoles) of H—Trp—Met—Asp—Phe—OGly—OH, prepared as described in Example 6, Step 9, and 0.23 g (0.60 mmoles) of BOC—β—OAla—OPFP, prepared as described in Example 6, Step 12, are dissolved in 10 ml of DMF, and 0.14 ml (1.0 mmole) of triethylamine are added to the solution. After 3.5 hours the reaction mixture is evaporated in vacuo and the residue is solidified with ether. The crude product, weighing 0.31 g, is dissolved in a small amount of solvent mixture 6, the solution is poured onto a column filled with 20 g of silica gel, and the column is eluted with solvent mixture 6 at a rate of 5 ml/hour. The pure fractions are pooled, evaporated in vacuo, and the residue is isolated with dry ether. 0.14 g (34%) of amorphous, chromatographically uniform BOC—β—OAla—Trp—Met—Asp—Phe—OGly—OH are obtained; $R_f^6 = 0.1$, $R_f^7 = 0.3$.

Analysis: Calculated for $C_{39}H_{51}O_{13}N_7S$ (M,wt.: 857.94): C: 54.60%, H: 5.99%, N: 11.43%. Found: C: 54.40%, H: 6.10%, N: 11.27%.

EXAMPLE 7

2-(2-(tert.-Butoxycarbonyl-aminooxy)-acetyl-L-tryptophyl-L-methionyl-L-aspartyl-L-phenylalanyl-aminooxy)-acetic acid 0.34 g of H—Trp—Met—Asp—Phe—OGly—OH, prepared as described in Example 6, Step 9, are dissolved in 10 ml of DMF, and 0.14 ml (1 mmole) of triethylamine and 0.28 g (0.6 mmoles) of BOC—O—Gly—OPCP, prepared as described in Example 1, Step 9, are added to the solution. After 3 hours the reaction mixture is evaporated in vacuo and the crude product is solidified with ether. The crude product, weighing 0.43 g, is dissolved in a small amount of solvent mixture 6, the solution is poured onto a column filled with 20 g of silica gel, and the column is eluted with solvent mixture 6 at a rate of 10 ml/hour. The pure fractions are pooled and evaporated in vacuo. 0.15 g (31%) of amorphous BOC—OGly—Trp—Met—Asp—Phe—OGly—OH are obtained; $R_f^7 = 0.4$.

Analysis: Calculated for $C_{38}H_{49}O_{13}N_7S$ (M.wt.: 843.92): C: 54.08%, H: 5.85%, N: 11.61%. Found: C: 53.95%, H: 5.97%, N: 11.70%.

EXAMPLE 8

2-(2-D-(tert.-Butoxycarbonyl-aminooxy)-propionyl-L-tryptophyl-L-methionyl-L-aspartyl-L-phenylalanyl-aminooxy)-acetic acid 0.23 g (0.60 mmoles) of BOC—D—OAla—OPCP, prepared as described in Example 5, Step 4, and 0.34 g (0.50 mmoles) of H—Trp—Met—Asp—Phe—O-Gly—OH are dissolved in 10 ml of DMF, and 0.14 ml (1.0 mmole) of triethylamine are added to the solution. After 3 hours the reaction mixture is evaporated in vacuo, the residue is solidified with ether, and filtered off. The crude product, weighing 0.41 g, is dissolved in a small amount of solvent mixture 7, the solution is poured onto a column filled with 40 g of silica gel, and the column is eluted with solvent mixture 7 at a rate of 10 ml/hour. The pure fractions are pooled, evaporated in vacuo, and the residue is isolated with dry ether. 0.11 g (25.6%) of amorphous BOC—D—OAla—Trp—Met—Asp—Phe—OGly—OH are obtained; $R_f^7 = 0.25$.

Analysis: Calculated for $C_{39}H_{51}O_{13}N_7S$ (M.wt.: 857.94): C: 54.60%, H: 5.99%, N: 11.43%. Found: C: 54.41%, H: 5.87%, N: 11.32%.

EXAMPLE 9

2-(2-L-(tert.-Butoxycarbonyl-aminooxy)-propionyl-L-tryptophyl-L-methionyl-L-aspartyl-L-phenylalanyl-aminooxy)-acetic acid One proceeds as described in Example 8, with the difference that BOC—L—OAla—OPCP, prepared as described in Example 3, Step 1, is applied as starting substance. The crude product, weighing 0.38 g, is purified on silica gel. 0.13 g of chromatographically uniform BOC—L—OAla—Trp—Met—Asp—Phe—O-Gly—OH are obtained; $R_f^7 = 0.25$.

Analysis: Calculated for $C_{39}H_{51}O_{13}N_7S$ (M.wt.: 857.94): C: 54.60%, H: 5.99%, N: 11.43%. Found: C: 54.47%, H: 6.04%, N: 11.41%.

EXAMPLE 10

Step 1

N-tert.-Butoxycarbonyl-L-norleucine pentafluorophenyl ester 10.0g (24.3 mmoles) of BOC—Nle—OH.DCHA are added to a mixture of 75 ml of ether and 25 ml of 2 n aqueous sulfuric acid, and the mixture is shaken until the dissolution is complete. The phases are separated, and the etheral solution is washed again with 25 ml of 2 n aqueous sulfuric acid and water. The etheral solution is evaporated in vacuo. The resulting 5.44 g of oily residue and 4.42 g (24 mmoles) of pentafluorophenol are dissolved in 30 ml of ethyl acetate, the solution is cooled to 0° C., and 4.63 g (22.5 mmoles) of dicyclohexyl carbodiimide are added. The suspension is allowed to stand at a cold place for 1 hour, thereafter it is filtered, and the filtrate is evaporated in vacuo. The residue is dissolved in 50 ml of n-hexane and the solution is washed with 5×20 ml of 5% aqueous sodium bicarbonate solution and 2×20 ml of water. The organic solution is dried and evaporated in vacuo. The oily residue solidifies upon cooling. 8.12 g (91%) of BOC—Nle—OPFP are obtained; m.p.: 55°–57° C., $[\alpha]_D$: −26.8° (c=1.0, in dioxane), $R_f^2 = 0.80$, $R_f^4 = 0.85$.

Analysis: Calculated for $C_{17}H_{20}O_4NF_5$ (M.wt.: 397.35): C: 51.39%, H: 5.07%, F: 23.91%. Found: C: 51.51%, H: 4.68%, F: 24.06%.

Step 2

N-tert.-Butoxycarbonyl-L-norleucycl-L-aspartyl-(tert.-butyl ester)-L-phenylalanine-amide 1.68 g (5.0 mmoles) of H—Asp (O'Bu)—Phe—NH₂, prepared as described in Example 1, Step 4, and 2.2 (5.5 mmoles) of BOC—Nle—OPFP, prepared as described in Example 10, Step 1, are dissolved in 10 ml of DMF in the presence of 0.70 ml (5.0 mmoles) of triethylamine. After 3 hours the reaction mixture is evaporated in vacuo, the solid residue is admixed with ether and filtered when cold. 2.23 g (81.8%) of BOC—Nle—Asp-(O'Bu)—Phe—NH₂ are obtained; m.p.: 164°–165° C. A sample of the product is recrystallized from ethyl acetate; m.p.: 165°–167° C., $R_f^4 = 0.70$, $[\alpha]_D$: −2.2° (c=1.0, in dimethyl formamide).

Analysis: Calculated for $C_{28}H_{44}O_7N_4$ (M.wt.: 548.66): C: 61.29%, H: 8.08%, N: 10.24%. Found: C: 61.34%, H: 7.70%, N: 10.40%.

Step 3

L-Norleucyl-L-aspartyl-L-phenylalanine-amide hydrochloride 1.90 g (3.47 mmoles) of BOC—Nle—Asp(O'Bu)—Phe—NH₂ are dissolved in 15 ml of 4 n hydrochloric acid in acetic acid. After 1 hour the reaction mixture is evaporated in vacuo, and the solid residue is filtered with ether. 1.48 g (98%) of H—Nle—Asp—Phe—NH₂.HCl are obtained; $[\alpha]_D$: −15.4° (c=1.0, in dimethyl formamide), $R_f^7 = 0.35$. The product decomposes at 195° C.

Step 4

N-tert.-Butoxycarbonyl-L-tryptophyl-L-norleucyl-L-aspartyl-L-phenylalanine-amide 1.35 g (3.15 mmoles) of H—Nle—Asp—Phe—NH$_2$.HCl and 1.26 g (3.15 mmoles) of BOC—Trp—OSu are dissolved in 40 ml of DMF in the presence of 0.88 ml (6.3 mmoles) of triethylamine. The reaction mixture is stirred overnight, evaporated in vacuo, and the oily residue is solidified with a dilute aqueous acetic acid solution. The suspension is filtered when cold, and the precipitate is washed with water and ether. 1.92 g (89.7%) of BOC—Trp—Nle—Asp—Phe—NH$_2$ are obtained; $[\alpha]_D$: −28.8° (c=1.0, in dimethyl formamide), $R_f^5$=0.50. The product decomposes at 196° C. The product is applied in the next step without further purification.

Step 5

L-Tryptophyl-L-norleucyl-L-aspartyl-L-phenylalanine-amide hydrochloride 1.85 g (2.73 mmoles) of BOC—Trp—Nle—Asp—Phe—NH$_2$ are treated with 50 ml of 8 n hydrochloric acid in dioxane. After 1 hour the solution is evaporated in vacuo, the gelly residue is admixed with acetone, and filtered. 1.17 g (69.7%) of H—Trp—Nle—Asp—Phe—NH$_2$.HCl are obtained. The product decomposes at 235° C.; $[\alpha]_D$: −28.4°, $R_f^7$=0.55. The physical constants of the authentic sample [J. S. Morley and J. S. Smith: J. Chem. Soc. C 726 (1968)] are: decomposition point: 235° C., $[\alpha]_D$: −28.3° (c=1.0, in dimethyl formamide).

Step 6

2-D-(tert.-Butoxycarbonyl-aminooxy)-propionyl-L-tryptophyl-L-norleucyl-L-aspartyl-L-phenylalanine-amide 1.0 g (1.62 mmoles) of H—Trp—Nle—Asp—Phe—NH$_2$.HCl is reacted with 0.74 g (1.62 mmoles) of BOC—D—OAla—OPCP, prepared as described in Example 5, Step 4, in 10 ml of DMF in the presence of 0.68 ml (4.86 mmoles) of triethylamine. Next day the reaction mixture is evaporated in vacuo, the gelly residue is admixed with ether, filtered, and washed with ether and water. The crude product, weighing 1.36 g, is subjected to column chromatography using solvent mixture 10 as eluting agent. The pure fractions are pooled, evaporated in vacuo, the solid residue is admixed with 50% aqueous ethanol, and the mixture is filtered. 0.25 g of BOC—D—OAla—Trp—Nle—Asp—Phe—NH$_2$ are obtained; m.p.: 217°–218° C. (decomposition), $R_f^3$=0.30, $R_f^{10}$=0.15, $[\alpha]_D$= +4.3° (c=1.0, in dimethyl formamide).

Analysis: Calculated for $C_{38}H_{51}O_{10}N_7$(M.wt.: 765.88): C: 59.59%, H: 6.71%, N: 12.80%. Found: C: 59.40%, H: 6.55%, N: 12.83%.

EXAMPLE 11

Step 1

N-tert.-Butoxycarbonyl-L-norvaline pentafluorophenyl ester 8.0 g (20 mmoles) of BOC—Nva—OH.DCHA are added to a mixture of 60 ml of ether and 20 ml of 2 n aqueous sulfuric acid, and the mixture is shaken until dissolution is complete. The etheral solution is separated, washed with 20 ml of 2 n aqueous sulfuric acid and water, dried, and evaporated in vacuo. The oily residue and 3.70 g (20 mmoles) of pentafluorophenol are dissolved in 25 ml of ethyl acetate, the solution is cooled to 0° C., 3.92 g (19 mmoles) of DCC are added, and the reaction is conducted for one hour. Thereafter the suspension is filtered, the filtrate is evaporated in vacuo, and the oily residue is dissolved in 50 ml of n-hexane. The solution is washed with 5×20 ml of 5% aqueous sodium bicarbonate solution and 2×20 ml of water and evaporated in vacuo. The oily residue solidified upon cooling. 6.21 g (81%) of BOC—Nva—OPFP are obtained; m.p.: 60°–62° C., $R_f^3$=0.70, $[\alpha]_D$:−32.3° C. (c=1.0, in dioxane).

Analysis: Calculated for $C_{16}H_{18}O_4NF_5$(M.wt.: 383.32): C: 50.14%, H: 4.73%, F: 24.78%. Found: C: 50.06%, H: 4.64%, F: 24.63%.

Step 2

N-tert.-Butoxycarbonyl-L-norvalyl-L-aspartyl-β-(tert.-butyl ester)-L-phenylalanine-amide 1.68 g (5.0 mmoles) of H—Asp(O$^t$Bu)—Phe—NH$_2$, prepared as described in Example 1, Step 4, are reacted with 2.12 g (5.5 mmoles) of BOC—Nva—OPFP in 10 ml of DMF in the presence of 0.70 ml (5 mmoles) of triethylamine. After 4 hours the reaction mixture is evaporated in vacuo and the oily residue is solidified with ether. 2.30 g (86.2 %) of BOC—Nva—Asp(O$^t$Bu)—Phe—NH$_2$ are obtained; m.p.: 169°–170° C., $R_f^4$=0.65, $[\alpha]_D$: −41.6° (c=1.0, in methanol).

Analysis: Calculated for $C_{27}H_{42}O_7N_4$ (M.wt.: 534.64): C: 60.65%, H: 7.92%, N: 10.48%. Found: C: 60.60%, H: 7.77%, N: 10.33%.

Step 3

L-Norvalyl-L-aspartyl-L-phenylalanine-amide hydrochloride 1.90 g (3.55 mmoles) of BOC—Nva—Asp(O$^t$Bu)—Phe—NH$_2$ are treated with 10 ml of 4 n hydrochloric acid in acetic acid for 1 hour. The solution is evaporated, the solid residue is admixed with ether, and the mixture is filtered. 1.45 g (98.3%) of H—Nva—Asp—Phe—NH$_2$.HCl are obtained; $[\alpha]_D$: −15.0° (c=1.0, in dimethyl formamide), $R_f^7$=0.15. The product decomposes at 204° C.

Step 4

N-tert.-Butoxycarbonyl-L-tryptophyl-L-norvalyl-L-aspartyl-L-phenylalanine-amide 1.24 g (3.0 mmoles) of H—Nva—Asp—Phe—NH$_2$.Cl are reacted with 1.20 g (3.0 mmoles) of BOC—Trp—OSu in 15 ml of DMF in the presence of 0.84 ml (6.0 mmoles) of triethylamine. Next day the reaction mixture is evaporated in vacuo and the residue is solidified with water. The suspension is filtered, and the filter cake is washed with a great proportion of water. The resulting crude product, weighing 2.0 g, is recrystallized from 30 ml of 80% ethanol. 1.47 g (73.9%) of BOC—Trp—Nva—Asp—Phe—NH$_2$ are obtained; m.p.: 207°–208° C., $R_f^5$32 0.35, $[\alpha]_D$: −43.4° (c=1.0, in dimethyl formamide).

Analysis: Calculated for $C_{34}H_{44}O_8N_6$ (M.wt.: 664.77): C: 61.43%, H: 6.67%, N: 12.64%. Found: C: 61.37%, H: 6.80%, N: 12.57%.

Step 5

L-Tryptophyl-L-norvalyl-L-aspartyl-L-phenylalanine-amide hydrochloride 1.80 g (2.72 mmoles) of BOC—Trp—Nva—Asp—Phe—NH$_2$ are treated with 20 ml of 4 n hydrochloric acid in dioxane in the presence of 0.98 ml (14 mmoles) of mercaptoethanol. After 15 minutes the solution is evaporated in vacuo, the solid residue is admixed with ether, and the mixture is filtered. 1.67 g (98.0%) of H—Trp—Nva—Asp—Phe—NH$_2$.HCl are obtained; m.p.: 200°–202° C., R$_f^7$=0.25, [α]$_D$: −30.0° (c=1.0, in dimethyl formamide).

Step 6

2-D-(tert.-Butoxycarbonyl-aminooxy)-propionyl-L-tryptophyl-L-norvalyl-L-aspartyl-L-phenylalanine-amide 1.55 g (2.52 mmoles) of H—Trp—Nva—Asp—Phe—NH$_2$.HCl are reacted with 1.14 g 2.52 mmoles) of BOC—D—OAla—OPCP, prepared as described in Example 5, Step 4, in 20 ml of DMF in the presence of 1.06 ml (7.56 mmoles) of triethylamine. Next day the reaction mixture is evaporated in vacuo, the residue is admixed with water, and the mixture is filtered. The precipitate is washed with water and ether. The crude product, weighing 2.36 g, is chromatographed on a silica gel column, using solvent mixture 10 as eluting agent. 0.82 g (43.4%) of BOC—D—OAla—Trp—Nva—Asp—Phe—NH$_2$ are obtained; m.p.: 220°–221° C (decomposition), R$_f^{10}$=0.20, R$_f^5$=0.30, [α]$_D$: +3.7° (c=1.0, in dimethyl formamide).

Analysis: Calculated for C$_{37}$H$_{49}$O$_{10}$N$_7$ (M.wt.: 751.85): C: 59.11%, H: 6.57%, N: 13.04%. Found: C: 59.57%, H: 6.70%, N: 13.21%.

EXAMPLE 12

Step 1

2-L-(tert.-Butoxycarbonyl-amino)-decanoic acid pentafluorophenyl ester 4.25 g (14.7 mmoles) of BOC—Ade—OH and 2.94 g (16.0 mmoles) of pentafluorophenol are dissolved in 40 ml of ethyl acetate, and 2.99 g (14.5 mmoles) of DCC are added to the solution at 0° C. The reaction mixture is stirred for one hour at room temperature and for one hour at 0° C. The separated DCU is filtered off, the filtrate is evaporated in vacuo, and the oily residue is dissolved in 40 ml of n-hexane. The solution is washed with 5×20 ml of 5% aqueous sodium bicarbonate solution and 2×20 ml of water, dried, and evaporated in vacuo. The oily residue solidified upon cooling. 5.82 g (87.5%) of BOC—L—Ade—OPFP are obtained; m.p.: 45°–46° C., R$_f^2$=0.85, [α]$_D$: −18.1° (c=1.0, in dioxane).

Analysis: Calculated for C$_{21}$H$_{28}$O$_4$NF$_5$ (M.wt.: 434.45): C: 55.63%, H: 6.22%, F: 20.95%. Found: C: 55.56%, H: 5.96%, F: 20.89%.

Step 2

2-L-(tert.-Butoxycarbonyl-amino)-decanoyl-L-aspartyl-(tert.-butyl ester)-L-phenylalanine-amide 1.0 g (3.0 mmoles) of H—Asp(O$^t$Bu)—Phe—NH$_2$, prepared as described in Example 1, Step 4, is reacted with 1.36 g (3.0 mmoles) of BOC—Ade—OPFP in 10 ml of DMF, in the presence of 0.42 ml (3.0 mmoles) of triethylamine. After 1.5 hours the reaction mixture is evaporated in vacuo and the residue is solidified with ether. The suspension is filtered when cold. 1.65 g (90.8%) of BOC—L—Ade—Asp(O$^t$Bu)—Phe—NH$_2$ are obtained, m.p.: 142°–143° C., R$_f^4$=0.70, [α]$_D$: −32.4° (c=1.0, in dimethyl formamide).

Analysis: Calculated for C$_{32}$H$_{52}$O$_7$N$_4$ (M.wt.: 604.77): C: 63.55%, H: 8.67%, N: 9.27%. Found: C: 63.34%, H: 8.70%, N: 9.26%.

Step 3

2-L-Amino-decanoyl-L-aspartyl-L-phenylalanine-amide hydrochloride 1.45 g (2.39 mmoles) of BOC—L—Ade—Asp(O$^t$-Bu)—Phe—NH$_2$ are treated with 15 ml of 4 n hydrochloric acid in acetic acid. After 1 hour the solution is evaporated in vacuo and the solid residue is admixed with ether. The mixture is filtered. 1.03 g (88.9%) of H—L—Ade—Asp—Phe-NH$_2$.HCl are obtained; m.p.: 180°–181° C., R$_f^7$=0.35, [α]$_D$: −12.1° (c=1.0, in dimethyl formamide).

Step 4

N$_α$-tert.-Butoxycarbonyl-N$_{ind}$-formyl-L-tryptophyl-2-L-amino-decanoyl-L-aspartyl-L-phenylalanine-amide 0.90 g (1.86 mmoles) of H—L—Ade—Asp—Phe—NH$_2$.HCl is reacted with 0.93 g (1.86 mmoles) of BOC-Trp(For)OPFP in 15 ml of DMF in the presence of 0.52 ml (3.72 mmoles) of triethylamine. Next day the reaction mixture is evaporated in vacuo and the residue is solidified with water. The suspension is filtered and the precipitate is washed with water and ether. 1.20 g (87.5) of BOC-Trp(For)-L-Ade-Asp-Phe-NH$_2$are obtained, m.p.: 204° C. (decomposition), [α]$_D$: −29.1° (c=1.0, in dimethyl formamide), R$_f^5$=0.45.

Analysis: Calculated for C$_{40}$H$_{54}$O$_8$N$_6$ (M.wt.: 762.88): C: 62.97%., H: 7.14%, N: 11.02%. Found: C: 62.71%, H: 7.14%, N: 11.06%.

Step 5

L-Tryptophyl-2-L-amino-decanoyl-L-aspartyl-L-phenyl-alanine-amide hydrochloride 1.05 g (1.37 mmoles) of BOC—(For)—L—Ade—Asp—Phe—NH$_2$ are treated with 10 ml of 4 n hydrochloric acid in dioxiane in the presence of 0.49 ml (7.0 mmoles) of mercaptothanol. After 14 minutes the reaction mixture is evaporated in vacuo and the residue is filtered in the presence of ether. 0.91 g (99%) of H-Trp—L—Ade—Asp—Phe—NH$_2$.HCl are obtained; m.p. 240° C. (decomposition), [α]$_D$= −25,6° (c=1,0, in dimethyl formamide), R$_f^7$=0.40.

Step 6 tert.-Butoxycarbonyl-aminooxy-acetyl-L-tryptophyl-2-L-amino-decanoyl-L-aspartyl-L-phenylalanine-amide 0.85 g (1.22 mmoles) of H—Trp—L—Ade—Asp—Phe—NH$_2$.HCl are reacted with 0.54 g (1.22 mmoles) of BOC—OGly—OPFP, prepared as described in Example 1, Step 9, in 10 ml of DMF in the presence of 0.51 ml (3.66 mmoles) of triethylamine. Next day the reaction mixture is evaporated in vacuo, the residue is solidified with water, the suspension is filtered, and the precipitate is washed with water and ether. The crude product, weighing 0.95 g, is subjected to column chromatography on silica gel, using solvent mixture 10 as eluting agent. The pure fractions are evaporated to obtain 0.43 g of BOC—OGly—Trp—L—Ade—Asp—Phe—NH$_2$, m.p.: 216°–217° C. (decomposition), $R_f^5 = 0.35$, $R_f^{10} = 0.25$, $[\alpha]_D$: $-18.7°$ (c = 1.0, in dimethyl foramide).

Analysis: Calculated for $C_{41}H_{57}O_{10}N_7$ (M.wt.: 808.01): C: 60.95%, H: 7.71%, N: 12.13%. Found: C: 60.92%, H: 7.07%, N: 12.09%.

EXAMPLE 13

Step 1

2-D-(tert.-Butoxycarbonyl-amino)-decanoic acid pentafluorophenyl ester

One proceeds exactly as described in Example 12, Step 1, with the difference that the D isomer is used as a starting substance. The title product, melting at 45°–46.5° C., is obtained with a yield of 75.0%. $R_f^2 = 0.85$, $[\alpha]_D$: $+18.1°$ (c = 1.0, in dioxane).

Step 2

2-D-(tert.-Butoxycarbonyl-amino)-decanoyl-L-aspartyl-β-(tert.-butyl ester)-L-phenylalanine-amide 1.20 g (3.37 mmoles) of H—Asp(O'Bu)—Phe—NH₂, prepared as described in Example 1, Step 4, are reacted with 1.49 g (3.5 mmoles) of BOC—D—Ade—OPFP in 10 ml of DMF in the presence of 0.49 ml (3.5 mmoles) of triethylamine. Next day the reaction mixture is evaporated in vacuo, the residue is admixed with diisopropyl ether, and the mixture is filtered. 1.26 g (61.8%) of BOC—D—Ade—Asp(O'Bu)—Phe—NH₂ are obtained; m.p.: 168°–170° C., $R_f^4 = 0.80$, $[\alpha]_D$: $-36.9°$ (c = 1.0, in dimethyl formamide).

Analysis: Calculated for $C_{32}H_{52}O_7N_4$ (M.wt.: 604.77): C: 63.55%, H: 8.67%, N: 9.27%. Found: C: 63.70%; H: 8.80%, N: 9.52%.

Step 3

2-D-Amino-decanoyl-L-aspartyl-L-phenylalanine-amide hydrochloride 1.10 g (1.82 mmoles) of BOC—D—Ade—Asp(O'Bu)—Phe—NH₂ are treated with 12 ml of 4 n hydrochloric acid in acetic acid. After 1 hour the reaction mixture is evaporated in vacuo, the solid residue is admixed with ether, and the mixture is filtered. 0.87 g (99%) of H—D—Ade—Asp—Phe—NH₂.HCl are obtained: $R_f^7 = 0.50$, $[\alpha]_D$: $-76.1°$ (c = 1.0, in dimethyl formamide). The substance decomposes at 198°–200° C.

Step 4

N-tert.-Butoxycarbonyl-L-tryptophyl-2-D-amino-decano-yl-L-aspartyl-L-phenylalanine-amide 0.80 g (1.65 mmoles) of H—D—Ade—Asp—Phe—NH₂.HCl are reacted with 0.80 g (1.70 mmoles) of BOC—Trp—OPFP in 10 ml of DMF in the presence of 0.70 ml (5.0 mmoles) of triethylamine. Next day the reaction mixture is evaporated in vacuo, and the residue is solidified with cold ether. The suspension is filtered and the precipitate is washed with ether, a dilute aqueous acetic acid solution and water. 1.01 g (83.8%) of BOC—Trp—D—Ade—Asp—Phe$_{NH2}$ are obtained; m.p.: 196° C. (decomposition), $R_f^5 = 0.50$, $[\alpha]_D$: $-55.6°$ (c = 1.0, in dimethyl formamide).

Analysis: Calculated for $C_{39}H_{54}O_8N_6$ (M.wt.: 734.87): C: 63.74%, H: 7.41%, N: 11.44%. Found: C: 63.68%, H: 7.30%, N: 11.40%.

Step 5

L-Tryptophyl-2-D-amino-decanoyl-L-aspartyl-L-phenylalanine-amide hydrochloride 0.90 g (1.22 mmoles) of BOC—Trp—D—Ade—Asp—Phe—NH₂ are treated with 10 ml of 4 n hydrochloric acid in dioxane in the presence of 0.43 ml (6.1 mmoles) of mercaptoethanol. After 10 minutes the reaction mixture is evaporated in vacuo, the residue is admixed with ether, and the mixture is filtered. 0.75 g (91.4%) of H—Trp—D—Ade—Asp—Phe—NH₂.HCl are obtained; m.p.: 205°–207° C. (decomposition), $R_f^7 = 0.45$, $[\alpha]_D$: $-23.1°$ (c = 1.0, in dimethyl formamide).

Step 6 tert.-Butoxycarbonyl-aminoxy-acetyl-L-tryptophyl-2-D-amino-decanoyl-L-aspartyl-L-phenylalanine-amide 0.69 g (1.02 mmoles) of H—Trp—D—Ade—Asp—Phe—NH₂.HCl are reacted with 0.45 g (1.10 mmoles) of BOC—OGly—OPCP, prepared as described in Example 1, Step 9, in 10 ml of DMF in the presence of 0.42 ml (3.0 mmoles) of triethylamine. Next day the reaction mixture is evaporated in vacuo, the residue is solidified with water, the resulting suspension is filtered, and the precipitate is washed with water and ether. The obtained crude product, weighing 0.63 g, is subjected to column chromatography on silica gel, using solvent mixture 10 as eluting agent. 0.45 of BOC—OGlyTrp—D—Ade—Asp—Phe—NH₂ are obtained; m.p.: 162°–165° C. (decomposition), $R_f^5 = 0.60$, $R_f^{10} = 0.40$, $[\alpha]_D$: $-17.6°$ (c = 1.0, in dimethyl formamide).

Analysis: Calculated for $C_{41}H_{57}O_{10}N_7$ (M.wt.: 808.01): C: 60.95%, H: 7.11%, N: 12.13%. Found: C: 60.71%, H: 7.20%, N: 12.12%.

What we claim is:

1. A peptide of the formula:

A—Trp—B—Asp—Phe—NH—Y wherein

A is tert.-butoxycarbonyl-aminooxy-acyl, benzyloxycarbonyl-aminooxy-acyl, (aminooxy)-acyl or E-aminooxy-acyl, wherein E is benzoyl or straight-chain or branched $C_{1-5}$ aliphatic acyl, B is methionyl, leucyl, norleucyl, norvalyl or 2-amino-decanoyl, and Y is hydrogen or carboxymethoxy, a pharmaceutically acceptable acid-addition salt or complex thereof.

2. (tert.-Butoxycarbonyl-aminooxy)-acetyl-L-tryptophyl-L-methionyl-L-aspartyl-L-phenylalanine-amide.

3. (Aminooxy)-acetyl-L-tryptophyl-L-methionyl-L-aspartyl-L-phenylalanine-amide.

4. 2-(tert.-Butoxycarbonyl-aminooxy)-L-propionyl-L-tryptophyl-L-methyionyl-L-aspartyl-L-phenylalanine-amide.

5. 2-(tert.-Butoxycarbonyl-aminooxy)-acetyl-L-tryptophyl-L-leucyl-L-aspartyl-L-phenylalanine-amide.

6. 2-D-(tert.-Butoxycarbonyl-aminooxy)-propionyl-L-tryptophyl-L-leucyl-L-aspartyl-L-phenylalanine-amide.

7. 2-[3-(tert.-Butoxycarbonyl-aminooxy)-propionyl-L-tryptophyl-L-methionyl-L-aspartyl-L-phenylalanyl-aminooxy]-acetic acid.

8. 2-D-(tert.-Butoxycarbonyl-aminooxy)-propionyl-L-tryptophyl-L-norleucyl-L-aspartyl-L-phenylalanine-amide.

9. 2-(D-tert.Butoxycarbonyl-aminooxy)-propionyl-L-tryptophyl-L-norvalyl-L-aspartyl-L-phenylalanine-amide.

10. tert.-Butoxycarbonyl-aminooxy-acetyl-L-tryptophyl-2-L-amino-decanoyl-L-aspartyl-L-phenylalanine-amide.

11. tert.-Butoxycarbonyl-aminooxy-acetyl-L-tryptophyl-2-D-amino-decanoyl-L-aspartyl-L-phenylalanine-amide.

12. 2- [2-tert.-Butoxycarbonyl-aminooxy)-acetyl-L-tryptophyl-L-methionyl-L-aspartyl-L-phenylalanyl-aminooxy]-acetic acid.

13. 2-[2-D-(tert.-Butoxycarbonyl-aminooxy)-propionyl-L-tryptophyl-L-methionyl-L-aspartyl-L-phenylalanyl-aminooxy]-acetic acid.

14. 2-[2-L-(tert.-Butoxycarbonyl-aminooxy)-propionyl-L-tryptophyl-L-methionyl-L-aspartyl-L-phenylalanyl-aminooxy]-acetic acid.

15. A method for increasing gastric acid secretions which comprises the step of administering an effective amount of a compound according to claim 1.

16. The method according to claim 15 wherein the compound is enterally administered.

17. A composition for increasing gastric acid secretion consists essentially of at least one compound according to claim 1 in a pharmaceutically acceptable vehicle.

18. A composition according to claim 17 wherein said vehicle is selected from enterally administerable compatible vehicles.

19. A compound selected from the group consisting of:

(tert.-butoxycarbonyl-aminooxy)-acetyl-L-tryptophyl-L-methionyl-L-aspartyl-L-phenylalanine-amide;

(aminooxy)-acetyl-L-tryptophyl-L-methionyl-L-aspartyl-L-phenylalanine-amide;

2-(tert.-butoxycarbonyl-aminooxy)-L-propionyl-L-tryptophyl-L-methionyl-L-aspartyl-L-phenylalanine-amide;

2-(tert.-butoxycarbonyl-aminooxy)-acetyl-L-tryptophyl-L-leucyl-L-aspartyl-L-phenylalanine-amide;

2-D-(tert.-butoxycarbonyl-aminooxy)-propionyl-L-tryptophyl-L-leucyl-L-aspartyl-L-phenylalanine-amide;

2-[3-(tert.-butoxycarbonyl-aminooxy)-propionyl-L-tryptophyl-L-methionyl-L-aspartyl-L-phenylalanyl-aminooxy]-acetic acid;

2-D-(tert.-butoxycarbonyl-aminooxy)-propionyl-L-tryptophyl-L-norleucy-L-aspartyl-L-phenylalanine-amide;

2-D-(tert.-butoxycarbonyl-aminooxy)-propionyl-L-tryptophyl-L-norvalyl-L-aspartyl-L-phenylalanine-amide;

(tert.-butoxycarbonyl-aminooxy)-acetyl-L-tryptophyl-2-L-amino-decanoyl-L-aspartyl-L-phenylalanine-amide;

(tert.butoxycarbonyl-aminooxy)-acetyl-L-tryptophyl-2-D-amino-decanoyl-L-aspartyl-L-phenylalanine-amide;

2-[2-(tert.-butoxycarbonyl-aminooxy)-acetyl-L-tryptophyl-L-methionyl-L-aspartyl-L-phenylalanyl-aminooxy]-acetic acid;

2-[2-D-(tert.-butoxycarbonyl-aminooxy)-propionyl-L-tryptophyl-L-methionyl-L-aspartyl-L-phenylalanyl-aminooxy]-acetic acid; and 2-[2-L-(tert.butoxycarbonyl-aminooxy)-propionyl-L-tryptophyl-L-methionyl-L-aspartyl-L-phenylalanyl-aminooxy]-acetic acid and the acid-addition salts and complexes thereof.

* * * * *